(12) United States Patent
Stephenson et al.

(10) Patent No.: US 7,827,854 B2
(45) Date of Patent: Nov. 9, 2010

(54) METHOD AND KIT FOR ADSORBENT PERFORMANCE EVALUATION

(75) Inventors: Neil Andrew Stephenson, East Amherst, NY (US); Phillip Alexander Barrett, Tonawanda, NY (US); Steven J. Pontonio, Eden, NY (US); Michael T. Freiert, Tonawanda, NY (US); Jesus Gallego-Preciado Nieto, Grand Island, NY (US)

(73) Assignee: Praxair Technology, Inc., Danbury, CT (US)

( * ) Notice: Subject to any disclaimer, the term of this patent is extended or adjusted under 35 U.S.C. 154(b) by 349 days.

(21) Appl. No.: 12/166,061

(22) Filed: Jul. 1, 2008

(65) Prior Publication Data

US 2010/0000305 A1    Jan. 7, 2010

(51) Int. Cl.
*G01N 5/00* (2006.01)
(52) U.S. Cl. .................. 73/73; 96/417; 96/422
(58) Field of Classification Search .......... 73/73; 96/108–154, 228, 417, 422
See application file for complete search history.

(56) References Cited

U.S. PATENT DOCUMENTS

| | | | |
|---|---|---|---|
| 3,756,782 A | 9/1973 | Phillips | |
| 4,214,011 A * | 7/1980 | Strube | 426/591 |
| 4,237,726 A | 12/1980 | Peterson et al. | |
| 4,597,778 A * | 7/1986 | Szonntagh | 95/26 |
| 4,744,221 A * | 5/1988 | Knollmueller | 62/46.1 |
| 5,013,335 A * | 5/1991 | Marcus | 95/128 |
| 5,069,887 A * | 12/1991 | Suenaga et al. | 95/128 |
| 5,112,590 A * | 5/1992 | Krishnamurthy et al. | 423/418.2 |
| 6,772,536 B2 * | 8/2004 | Ely et al. | 34/380 |
| 2004/0069144 A1 * | 4/2004 | Wegeng et al. | 95/106 |
| 2006/0245994 A1 * | 11/2006 | Watanabe et al. | 423/305 |
| 2007/0004591 A1 * | 1/2007 | Itabashi et al. | 502/414 |

FOREIGN PATENT DOCUMENTS

| | | |
|---|---|---|
| EP | 0 484 121 A1 | 5/1992 |
| FR | 2 652 899 | 4/1991 |
| JP | 3110444 | 5/1991 |

* cited by examiner

*Primary Examiner*—David A. Rogers
(74) *Attorney, Agent, or Firm*—Salvatore P. Pace (57) ABSTRACT

The present invention generally relates to methods and kits for measuring and analyzing degradation of adsorbent materials, particularly for adsorbent materials used in gas separation processes. The present invention can assess the damage to adsorbent due to moisture contamination and it can assess damage that is not moisture-related. The advantage to the present invention is that it can detect degradation of adsorbent before the degradation affects production. Another advantage is that it can conclusively determine whether the sieve is damaged. Because it is so inexpensive to run, the test of the present invention can be conducted to determine adsorbent damage and to confirm whether the damage continues to be an issue. The present invention can test adsorbents in any form, including, but not limited to, bead, pellet or powder form.

17 Claims, 4 Drawing Sheets

METHOD AND KIT FOR ADSORBENT PERFORMANCE EVALUATION

FIELD OF THE INVENTION

The present invention generally relates to methods and kits for measuring and analyzing degradation of adsorbent materials, particularly for adsorbent materials used in gas separation processes.

BACKGROUND OF THE INVENTION

Gas separation is accomplished by processes such as pressure swing adsorption (PSA), vacuum swing pressure adsorption (VPSA), and temperature swing adsorption (TSA). These processes use vessels or beds containing one or more layers of adsorbent materials that adsorb one or more unwanted gases and produce the desired product gas. During the process cycle, the adsorbent materials adsorb the unwanted gases and then are regenerated by the removal of the unwanted gases by pressure, vacuum or temperature swings. Typical adsorbents used in these processes include zeolites, alumina and silica and combinations thereof.

Repeated use of an adsorbent causes degradation and eventually renders the adsorbent materials ineffective, such that the adsorbent materials need to be replaced periodically. Degradation of the adsorbent results in plant capacity decline and plant inefficiency, which is costly and time consuming. Often, adsorbent degradation is not detected until the product quality and/or overall plant performance is affected.

Currently, the testing of adsorbents is done by taking samples of the used adsorbent and subjecting them to various performance tests (including capacity measurements) and/or spectroscopic studies that are generally best performed in a laboratory or by a third party off-site. These methods of testing are slow and costly. It would be desirable to have a method of testing adsorbent degradation and quality that is quick and accurate and able to be conducted on-site at the separation plant.

The test methods currently in use include a Karl Fischer titration (KF) that determines trace amounts of water using potentiometric or coulometric titration. The application of KF methods to adsorbents such as zeolites requires system modifications whereby the sample is heated to high temperatures (about 1000° C.) and the water released is swept using a purge gas through a conventional KF cell. KF methods can specifically test for water content, unlike other loss on ignition (LOI) thermal methods that detect the loss of any volatile substance. However, the KF methods require the use of equipment that is very costly and not conducive to conducting the analysis outside of a laboratory, nor can they test for any other type of damage other than moisture damage.

LOI methods are based on the change in mass as a result of heating a sample under specified conditions. The LOI is expressed as a weight percentage of the dry mass. For example, a sample is heated in a furnace to a high temperature (e.g., 1000° C.) and the difference in mass before and after the ignition process is used to calculate the LOI. The LOI test measures the release of all volatiles which are adsorbed by the sample and cannot specifically test for moisture contamination or assess sample performance.

A near-infrared (NIR) moisture analyzer (e.g., Model #KJT-100, Kett US, Villa Park, Calif., USA) measures moisture levels based on the principle that water absorbs certain wavelengths of light. An optical filter is used to select a wavelength that either absorbs moisture (e.g., 1200, 1450 and 1950 nm) or does not absorb moisture (e.g., 1300 nm). This wavelength serves as a reference and incident radiation is reflected off a sample and measured by a lead sulfide (PbS) detector. The ratio of absorbed light to reference light is proportional to moisture content in the sample. Similar to KF titration, the NIR moisture analyzer only detects water and will not detect any other types of damage to the adsorbent and is very expensive.

An electronic moisture balance (e.g., Model #EB-340MOC, Shimadzu Corporation, Columbia, Md., USA) determines moisture content in solid substances using a thermogravimetric method. Far-infrared radiation is applied to the surface of a sample to heat it, then the sample is weighed upon drying and compared to the original weight. For many adsorbents such as zeolites, the output of the infrared heaters in commercial moisture balances is insufficient to remove all of the adsorbed water. Furthermore, the moisture balance can only detect moisture content and is very expensive.

Japanese Patent No. JP3110444 describes a method for measuring the adsorption performance of a solid adsorbent wherein a measuring gas containing the adsorption component is introduced into a vessel filled with the solid adsorbent. The measuring gas exits the vessel and goes through an analyzer that analyzes the amount of the adsorption component adsorbed by the solid material. This patent does not teach a method that can differentiate between moisture contamination and other damage to the adsorbent.

U.S. Pat. No. 4,237,726 (Peterson et al.) describes a process for predicting the useful life of a respirator cartridge wherein the process measures the weight increase of a sorptive agent when exposed to a gas mixture of dry air and a preselected organic vapor. In this process, the breakthrough time of the cartridge is determined by using the measured breakthrough time of the preselected vapor. As with the other processes described in the prior art, this process does not determine the damage to the sorptive agent and does not even measure moisture contamination of the sorptive agent.

The prior art and commercially available equipment all lack the capability of distinguishing between moisture contamination and any other type of damage to an adsorbent. Most of the prior art also involves the use of cumbersome equipment that cannot be used on-site at a plant and the methods are time consuming, expensive and inefficient. Results of the currently used methods are frequently received after the plant adsorbents have been irreversibly damaged, resulting in an expensive reload of the adsorbent beds. A method is needed that can provide diagnostic results quickly, identify the cause of plant degradation at an early stage and allow plant engineers to effectively perform preventative maintenance procedures to ensure the integrity of the adsorbent materials.

BRIEF SUMMARY OF THE INVENTION

The present invention is directed to a method of detecting and evaluating performance degradation of an adsorbent on-site at a gas separation plant.

The present invention can assess the damage to adsorbent due to moisture contamination and it can assess damage that is not moisture-related. The advantage to the present invention is that it can detect degradation of adsorbent before the degradation affects production. Another advantage is that it can conclusively determine whether the sieve is damaged. Because it is so inexpensive to run, the test of the present invention can be conducted to determine adsorbent damage and to confirm whether the damage continues to be an issue. The present invention can test adsorbents in any form, including, but not limited to, bead, pellet or powder form.

One embodiment of the present invention is a method of determining gas capacity of an adsorbent material used in a gas separation process comprising the steps of:

a. taking a sample of the adsorbent material used in the gas separation process and placing the sample in a container means in a controlled environment;
b. weighing the sample of the adsorbent material in the controlled environment;
c. measuring the ambient temperature of the controlled environment;
d. flowing a dry gas into the controlled environment;
e. adsorbing the gas onto the sample of adsorbent material;
f. saturating the sample with a displacing agent and displacing the adsorbed gas from the sample of adsorbent material;
g. measuring the volume of gas released from the sample of adsorbent material; and
h. calculating the ratio of gas released to the weight of the sample.

Another embodiment of the present invention is a kit for practicing the method of the present invention, comprising:

a. an atmosphere control system;
b. a balance with readability of at least 0.01 g;
c. at least three sample transfer means with airtight lids;
d. at least three sample-containing means with airtight septa caps;
e. a displacing agent;
f. a displacing agent-containing means;
g. a valve means;
h. a sample transfer means;
i. a sealing device;
j. at least one cannula; and
k. a thermometer.

BRIEF DESCRIPTION OF THE DRAWINGS

For a more complete understanding of the present invention and the advantages thereof, reference should be made to the following Detailed Description taken in conjunction with the accompanying drawings in which.

DETAILED DESCRIPTION OF THE INVENTION

The present invention is a method of detecting and evaluating performance degradation of an adsorbent on-site at a gas separation plant by determining the gas capacity of the adsorbent, said method comprising the steps of:

(a) obtaining at least one representative sample of adsorbent from adsorbent vessels in a gas separation plant;
(b) placing said sample in a controlled atmosphere, such as a secondary atmosphere control device;
(c) weighing said sample in the controlled atmosphere;
(d) measuring the ambient temperature in the controlled atmosphere;
(e) saturating said sample with a test gas in the controlled atmosphere;
(f) desorbing the test gas from the sample;
(g) measuring the amount of test gas desorbed from the sample; and
(h) comparing measurements obtained for sample with measurements for an ideal adsorbent material at the same ambient temperature.

In this specification, the terms "adsorbent", "adsorbent material", "molecular sieve" and "sieve" may be used interchangeably to mean the adsorbent material used in a gas separation process. The terms "adsorbent vessel" and "adsorbent bed" may be used interchangeably to mean the vessels in a gas separation plant packed with adsorbent material. The term "ideal adsorbent material" as used herein means adsorbent material that is the same type of material as the adsorbent sample, but that has not yet been used and is uncontaminated and undamaged. The term "syringe" as used herein means a simple piston pump consisting of a plunger that fits tightly in a tube. The plunger can be pulled and pushed along inside a cylindrical tube (the barrel), allowing the syringe to take in and expel a liquid or gas through an orifice at the open end of the tube. The open end of the syringe may be fitted with a hypodermic needle, cannula, nozzle, or tubing to help direct the flow into and out of the barrel. In this specification, the term "cannula" is used interchangeably with "needle" to describe a tube which can be inserted through a barrier (such as a septa cap) for the delivery or removal of a liquid or gas.

Another embodiment of the present invention is a field test kit for use in evaluating performance degradation of an adsorbent comprising the following:

One (1) atmosphere control system (e.g., Glove Bag™, Glas-Col, LLC, Terre Haute, Ind., USA)

One (1) balance with readability of 0.01 g (e.g., Blade V2-50, American Weigh Scales, Inc., Charleston, S.C., USA)

At least three (3) vials with airtight septa caps, capable of holding up to 2 g of adsorbent One (1) test cell (e.g., a glass syringe with free moving plunger up to 60 cc displacement, such as a 50 cc syringe, catalog #14-825-11A, from Fisher HealthCare, Houston, Tex., USA)

One (1) flow control device (e.g., a rotameter);

One (1) valve means for gas supply shut-off (e.g., ¼ inch ball valve);

One (1) scoopula or other device for sample transfer;

One (1) pair of cotton gloves (for use with atmosphere control system);

One (1) sealable container containing water;

One (1) sealing device (depending on atmosphere control system);

At least three (3) sample jars with airtight lids used to transfer adsorbent sample from vessel;

One (1) marker pen or other instrument for sample labeling;

One (1) or two (2) extra cannulae; and

One (1) thermometer.

The airtight septa caps and lids for the vials and sample jars should form an airtight seal and can be made of materials such as rubber or Teflon. The sealable container containing water should be spill-proof and keep the water inside. The container should be big enough to hold enough water to test at least three samples (e.g., at least 12 ml). Furthermore, in order to place items such as the balance into the atmosphere control system, a large opening is needed to insert the items. The sealing device is used to close up the opening to obtain a controlled atmosphere. Examples of acceptable sealing devices include, but are not limited to, a zip-lock closure, a zipper, or binder clips.

Figure 1:
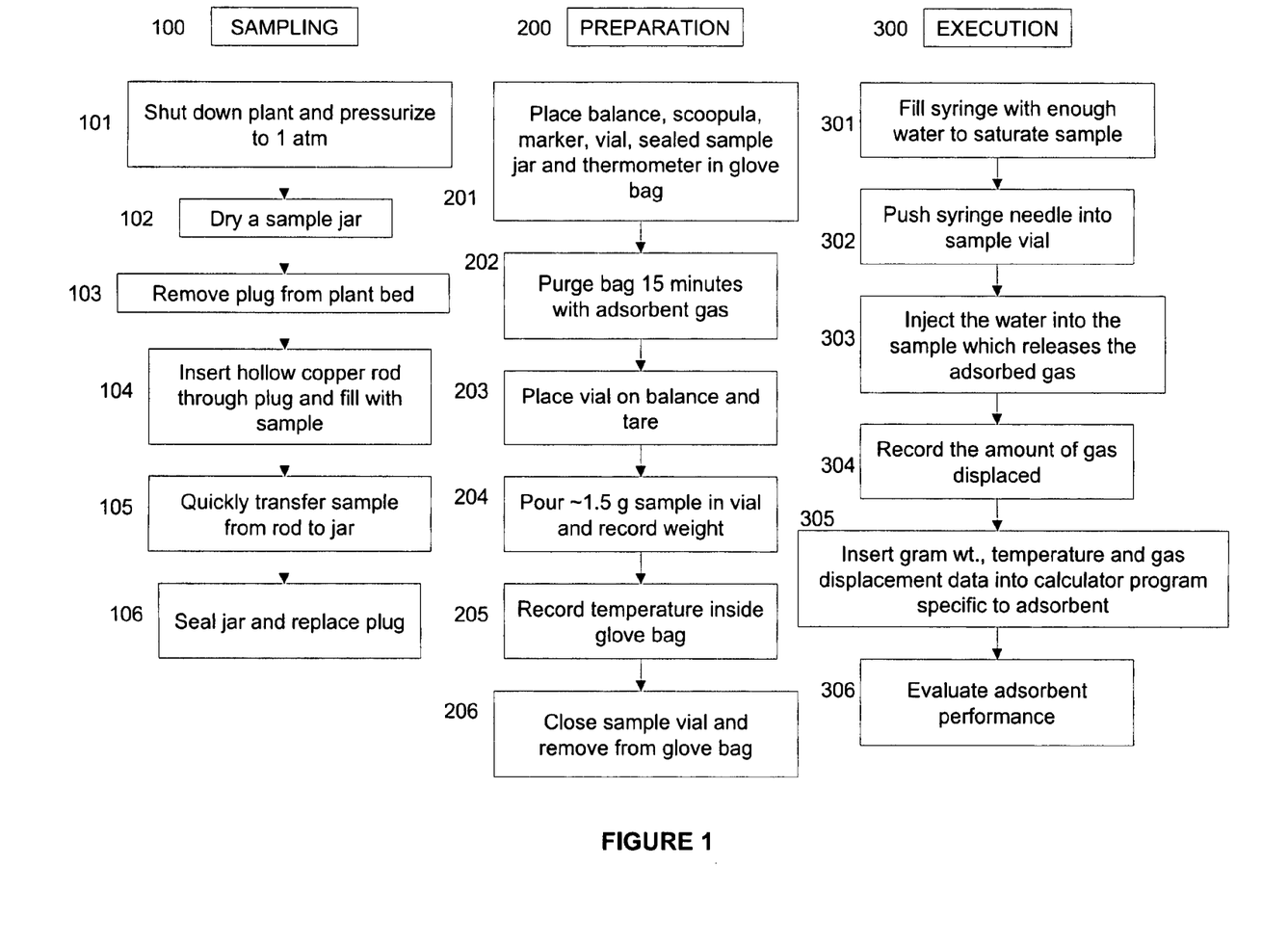
FIG. 1 is a schematic illustrating a workflow diagram for the test method of the present invention.

One embodiment of the present invention is a method of evaluating the performance degradation of an adsorbent on-site at a separation plant, wherein the method comprises a sampling stage, a test preparation stage and a test execution stage. FIG. 1 shows a flow chart consistent with implementing this embodiment of the present invention.

Stage 1: Sampling (100)

A sample of at least 1 g of adsorbent is first taken from an adsorbent vessel in a gas separation plant. It is critical that the sample is transferred from the vessel to a sample container without being exposed to the outside atmosphere. Adsorbents can be extremely hydrophilic and even a brief exposure to air can allow moisture to be adsorbed onto the sample. In order to achieve the most accurate test result, the sample must stay in the same condition during transfer as it was when sampled. Any moisture adsorbed during the transfer can affect the accuracy of the test. For example, for a VPSA plant using nitrogen-selective LiX adsorbent, an acceptable method for removing a sample from a VPSA adsorbent bed is as follows:

(a) Shut down the plant and pressurize the adsorbent bed to 1 atmosphere (101);

(b) Dry the sample jar by using a heat gun or by adding dry zeolite to the jar and then emptying the jar (102);

(c) Remove the plug from the adsorbent bed and cover immediately with duct tape or other sealing agent (103);

(d) Remove the duct tape and immediately push a thin-walled copper pipe into the center of the bed, then pull the pipe (filled with adsorbent material) from the bed and replace duct tape (104);

(e) Pour the adsorbent sample in the pipe into a dry sample jar (105); and (f) Secure an airtight lid onto the sample jar, remove the duct tape from the adsorbent bed and replace the plug (106).

It is important to take the adsorbent sample from the interior of the adsorbent bed to have a representative sample. The adsorbent material near the sampling port may be wetter than the majority of the adsorbent material in the bed. The sampling and sample handling procedure described herein is one example of an appropriate procedure. Any procedure that can maintain the integrity of the sample is appropriate for the present invention.

Stage 2: Test Preparation (200)

Prepare a source of a dry gas to be used as the test gas (e.g., N2, O2, air, CO2). The test gas should be one that is readily available in dry form and that will be appreciably adsorbed by the adsorbent. Place the balance, scoopula, marker, vials and thermometer in the atmosphere control system (201), then purge the system for at least 15 minutes with a dry gas (202). Place a vial on the balance and tare it (203). Place approximately 1.5 g of the adsorbent sample into the vial and record the precise weight of the sample (204). The sample will have adsorbed the dry test gas that was purged through the atmosphere control system. The sample must be big enough to provide significant results. A sample that is too small will have a margin of error that is too large and there will not be sufficient adsorption and displacement of the test gas. If the sample is too large, then the test cell will not be big enough to hold it. Thus, a sample in the range of 1.3 to 1.7 g is preferable. Record the temperature inside the atmosphere control system (205). Close the sample vial using a septa cap and remove the vial from the atmosphere control system (206).

Stage 3: Execution (300)

Figure 2:
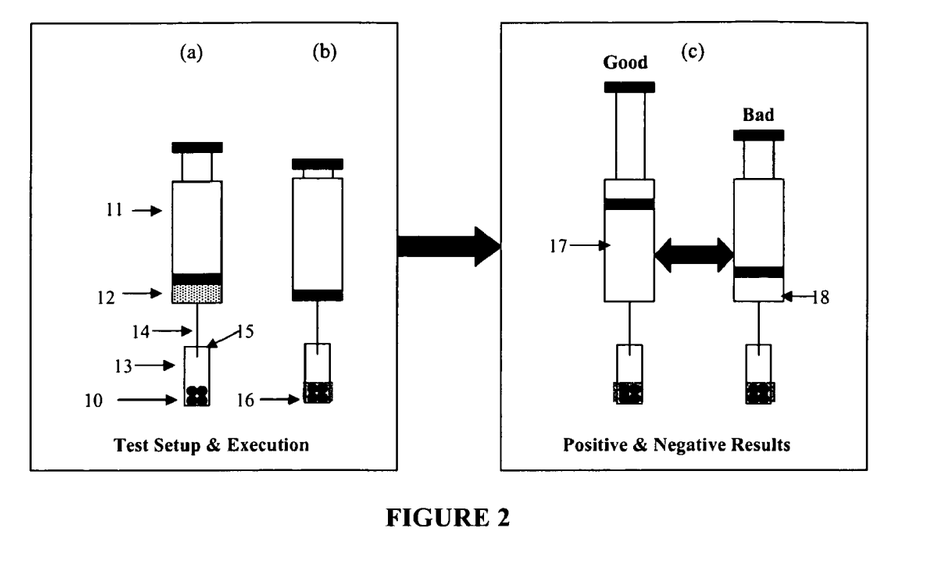
FIGS. 2(a) and 2(b) are schematics illustrating the test set-up and execution stages of the present invention, respectively.
FIG. 2(c) is a schematic illustrating good and bad test results obtained by using the present invention.

FIGS. 2(a) and 2(b) are graphical illustrations of the test set-up and execution stages, respectively, of the present invention. To displace the adsorbed test gas from the adsorbent sample (10), saturate the sample with a displacing agent, e.g., water. Attach a cannula (14) to the test cell (depicted in FIG. 2 as a syringe (11)) and fill it with enough water (12) to fully saturate the sample (301). For a sample of approximately 1.3 to 1.7 g, about 4 ml of water will be sufficient to saturate it. Insert the cannula into the sample vial (13) through the septa cap (15) (302) and inject the water into the sample vial (303). The water saturates the sample (16) and desorbs the test gas from the sample and the test gas is released from the sample back up through the cannula and collected in the syringe. FIG. 2(c) illustrates positive and negative results of the test. If a lot of test gas is released, the syringe will be filled (17), indicating that the adsorbent capacity is good. If very little test gas is released and the syringe is relatively empty (18), then the adsorbent capacity is bad. Although any appropriate apparatus that can contain and measure the test gas volume may be used as the test cell, the use of a glass syringe with water as the displacing agent is particularly effective because the water serves as a seal between the syringe barrel and the syringe plunger, making the syringe air tight.

Figure 3:
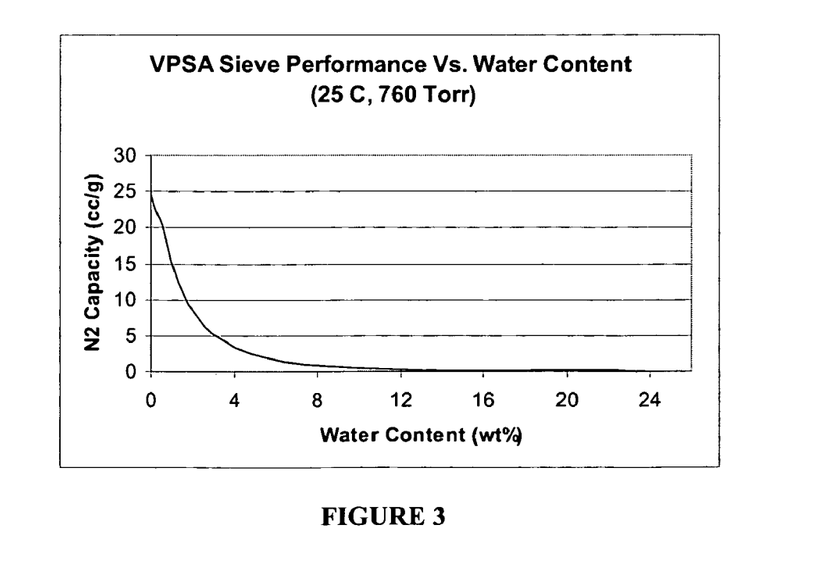
FIG. 3 is a graphical representation of the effect of water content on LiX2.0 performance.

The total volume of test gas collected in the syringe is recorded and noted (304). Each adsorbent type in its fully activated and undamaged state will adsorb a known amount of a certain gas. For example, highly exchanged (i.e., greater than 96%) lithium-exchanged zeolite X having a SiO2/Al2O3 ratio of 2 (LiX2.0) will adsorb 24 ml of nitrogen per gram of sample when fully activated and undamaged. Water contamination is one reason for degradation of LiX2.0 adsorbent performance in VPSA applications. For a given adsorbent, test gas and measurement temperature, a curve of performance versus % contaminant can be generated (see, e.g., FIG. 3). The displaced test gas volume per gram of sample is calculated from the measurements taken (i.e., displaced test gas volume (cc)/sample weight (g)). The calculated value for a specific temperature can be compared to a pre-generated curve such as that in FIG. 3 and the extent of contamination can be determined (305, 306). FIG. 3 illustrates the effect of water contamination on the adsorption capacity of LiX2.0 at a temperature of 25° C. The curve can be established experimentally for each adsorbent material for different temperatures by exposing the adsorbent to moisture and plotting the field test result (cc/g test gas capacity) versus Karl Fisher residual water test result.

Example 1

VPSA Field Test at Plant 1

A VPSA axial system, designated Plant 1, was not performing at normal capacity, possibly due to degradation of the zeolite adsorbent in the beds. The field test kit of the present invention was sent to Plant 1 to perform an on-site test to determine if there was any adsorbent degradation and whether the adsorbent degradation was the cause of the loss of plant capacity. Plant 1 contained two beds, A and B. Each bed was comprised of two different adsorbents, Adsorbent 1 and Adsorbent 2. Both adsorbents were lithium-exchanged type X zeolites. Adsorbent 1 had a $SiO_2/Al_2O_3$ ratio of 2 (LiX2.0) and Adsorbent 2 had $SiO_2/Al_2O_3$ ratio of 2.3 (LiX2.3). Adsorbent 2 was at the top of each bed and Adsorbent 1 was at the bottom of each bed.

Figure 4:
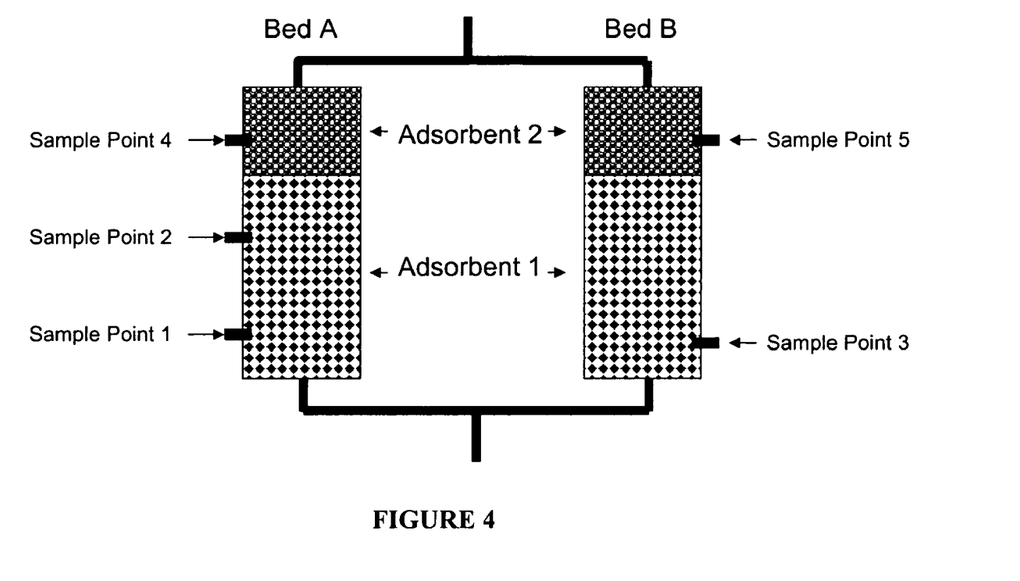
FIG. 4 is a schematic illustrating sampling points in two adsorbent beds.

The sampling and test procedures were as follows:

1. A total of five (5) samples were taken from the two beds. FIG. 4 shows the sample points where each of the samples was taken. Bed A was sampled at the top, middle and bottom (three locations; Sample Points 4, 2 and 1, respectively) and Bed B was sampled at the top and bottom (two locations; Sample Points 5 and 3, respectively). It is important to sample several locations in a bed because different locations in the bed may experience different amounts of adsorbent damage or contamination. The samples were handled in accordance with the method described herein, such that no additional contamination occurred during removal from the bed.

2. A dry nitrogen source was connected to a secondary atmosphere control device, such as an inflatable polyethylene glove chamber using plastic tubing. For this experiment, a Glove Bag™ (Glas-Col, LLC), was used as the secondary atmosphere control device. A rotameter was connected to the plastic tubing to control the nitrogen flow.

3. The samples obtained from the bed were placed in the glove chamber, together with the balance, vials, scoopula and a marker pen.

4. The glove chamber front opening was sealed using clips and the dry nitrogen was purged through at 4 splm for 15 minutes.

5. A vial without a cap was placed on the balance and tared. Using the scoopula, approximately 1.5 g of a sample was poured into the vial and the exact weight and sample identification number were recorded.

6. Step 5 was repeated for all of the other four samples.

7. The sealed vials containing the samples were removed from the glove chamber.

8. Four cc of water was aspirated into a 50 ml capacity glass syringe.

9. The syringe cannula was pushed through the septa cap of a sample vial and the water was injected into the sample, allowing the displaced gas to be transferred into the syringe. The amount of displaced gas transferred into the syringe was recorded. It should be noted that the release of gas upon water addition is extremely rapid and that significant pushback occurs during the injection. However, it is not critical that all of the water is injected in a single continuous step. The same results are obtained whether water is added in pulses or in one continuous injection.

10. Steps 8 and 9 were repeated for all of the other four samples.

The data for Example 1 are listed in Table 1.

TABLE 1

Water Detection Test Calculator; Test Gas: Nitrogen

| | Adsorbent Type | | | | |
|---|---|---|---|---|---|
| | Adsorbent 1 | | | Adsorbent 2 | |
| | Sample | | | | |
| | #1 | #2 | #3 | #4 | #5 |
| Bed | Bed A | Bed A | Bed B | Bed A | Bed B |
| Sample Point | Bottom T/C | Middle T/C | Bottom T/C | Top T/C | Top T/C |
| Weight of adsorbent sample (g) | 1.5 | 1.71 | 1.5 | 1.46 | 1.54 |
| Water added to syringe (ml) | 4 | 4 | 4 | 4 | 4 |
| Syringe reading after water injection (ml) | 32 | 35 | 26 | 12 | 20 |
| Calculated $N_2$ displaced per gram adsorbent (ml) | 18.67 | 18.71 | 14.67 | 5.48 | 10.39 |
| Calculated water in adsorbent (wt %) | 0.69 | 0.69 | 1.35 | 3.79 | 2.88 |

The results showed that the top of each bed had become partially deactivated by adsorbing moisture. Generally, a reading above approximately 0.8 wt % will have a great effect on the adsorbent performance. It was determined that the top of the beds were contaminated and the appropriate measures were taken to replace the contaminated adsorbent and optimize plant performance. It should be noted that the temperature in the glove chamber was measured for this experiment. However, it has been determined that the accuracy of the test can be improved still further by measuring the test temperature and accounting for the effect of this in the data analysis (i.e., using or deriving a curve at or close to (±2° C.) the test temperature). Therefore, temperature should be recorded and entered into the equation to be factored into the water content calculation.

Figure 5A:
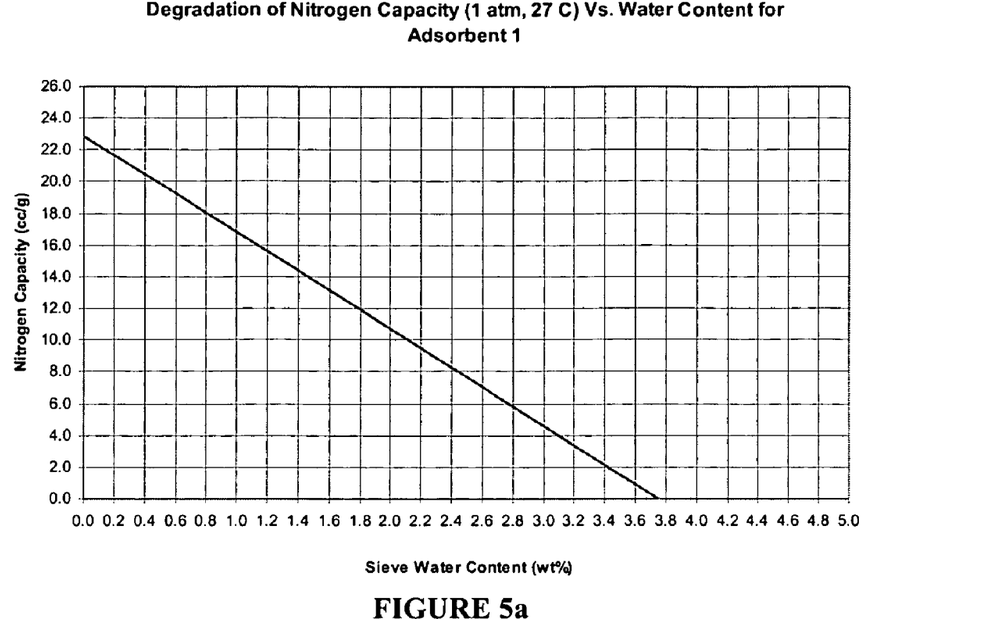
FIGS. 5(a) and 5(b) are graphical representations of the degradation of nitrogen capacity for Adsorbents 1 and 2, respectively.
Figure 5B:
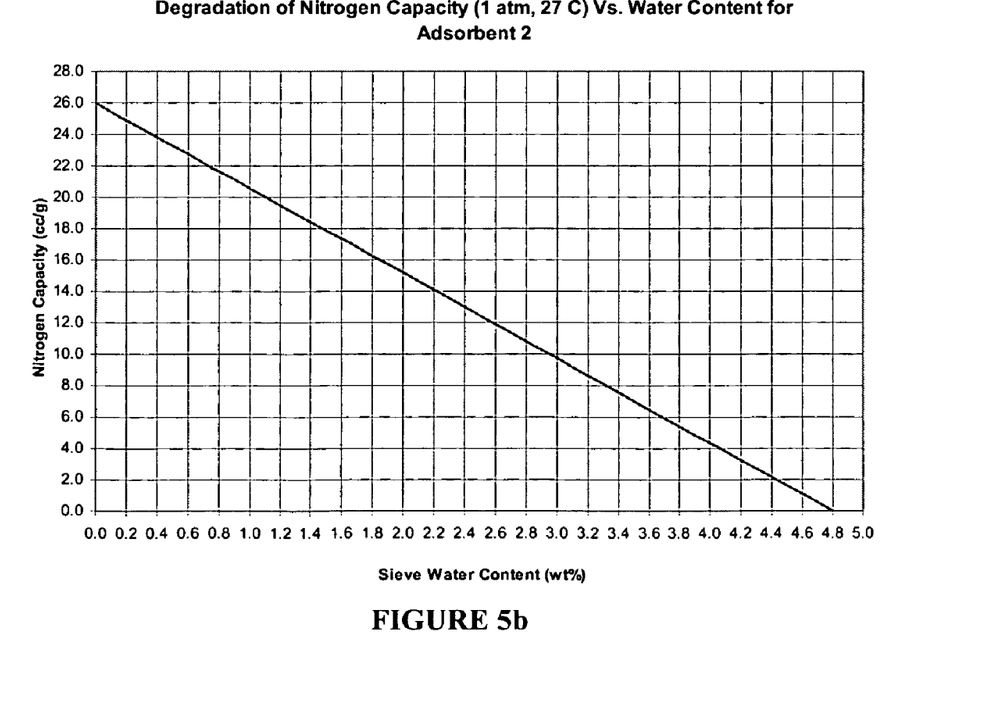

FIGS. 5a and 5b are graphical representations of the degradation of nitrogen capacity for Adsorbent 1 and Adsorbent 2, respectively, as the water content increases, measured at a pressure of 1 atm and a temperature of 27° C.

Example 2

Determination of Sieve Damage

Most adsorbent performance tests only detect moisture contamination. One embodiment of the present invention can test for sieve damage not related to moisture contamination. A sample of NaX zeolite having a $SiO_2/Al_2O_3$ ratio of 2.0 and in powder form was suspected of being damaged. The sample was tested according to the following method:

1. A glass test tube (open only at one end), equipped with a septa cap at the opening and two syringe needles were each weighed separately and the weights were recorded.

2. A sample of approximately 0.5 g was placed in the test tube and the test tube was sealed with the septa cap. The septa cap was then punctured with the two previously weighed needles. The sample must be sufficient to obtain significant adsorption and desorption of a test gas. This particular zeolite adsorbs 105 cc/g $CO_2$ at 27° C. If a 50 cc syringe is used, the sample size should be at 0.3 g, and preferably between 0.3 and 0.4 g. This will provide that an adsorption large enough to be accurate but small enough to stay within the syringe volume limit.

3. One of the needles was attached to a tube connected to a source of dry nitrogen and the other needle was left open to the atmosphere.

4. A flow of nitrogen was sent through the tube and into the test tube.

5. The sample was heated by ramping up to 400° C. in 1 hour and left at 400° C. for 30 minutes using a Vac Prep (Micromeritics Model 061). This activated the sample by driving out the water. It should be noted that a small layer of sample was used to allow for a more rapid activation without the concern of steaming, which could damage the zeolite.

6. The sample was then cooled, the flow of nitrogen was stopped, and the needles closed off to avoid contamination by moisture in the ambient air.

7. The test tube, adsorbent, septa cap and needles were weighed and the initial weight of these equipment was subtracted to determine the sample activated weight.

8. The sealed test tube containing the test sample was then brought back to the Vac Prep and one needle was attached to a tube connected to a dry $CO_2$ supply, which the other needle was left open to the atmosphere.

9. A flow of $CO_2$ was sent through the test tube and the $CO_2$ was adsorbed onto the sample. $CO_2$ is used because more volume is adsorbed so that despite the smaller sample size, a reasonable amount of gas can be measured.

10. After allowing the sample to reach equilibrium (approximately 10 minutes), the flow of $CO_2$ was stopped and the outlet needle was closed off.

11. The inlet needle was detached from the $CO_2$ source and attached to a glass syringe filled with 4 ml of water.

12. The water was injected into the test tube to displace the adsorbed $CO_2$ from the sample and force the displaced $CO_2$ back into the syringe. The displaced $CO_2$ was then measured.

NaX zeolite having a $SiO_2/Al_2O_3$ ratio of 2.0 should adsorb 105 cc/g of $CO_2$ at 27° C. if it is fully activated and undamaged. The sample was fully activated with a moisture content of less than 0.1 wt %, therefore any measured displacement below 105 cc/g signals sieve damage, with lower gas displacement signifying greater damage.

These examples demonstrate specific embodiments of the present invention. Another embodiment of the invention comprises a field test method as described herein, further comprising the use of more than one test gas, including but not limited to nitrogen, air or $CO_2$.

In another embodiment of the present invention, the method of measuring the displaced gas is to measure the pressure increase over a fixed volume. The adsorbent sample is contained in a sealed container with water or other displacing agent pumped in to saturate the adsorbent sample. The displaced gas would be released and subsequently increase the pressure inside the fixed volume container. A pressure gauge is used to measure the pressure increase. This result is then compared to a psi/g result for an ideal adsorbent which is uncontaminated and undamaged.

The displacing agent used in the above examples is water, but different displacing agents may also be used. Any agent that provides the displacement of the adsorbed test gas for measurement may be used, such as alcohol or any water-based liquid.

The method and kit of the present invention may be used to test many different types of adsorbent. Any adsorbent for which the ideal capacity of a gas is known or can be measured or calculated can be tested using the method and kit of the present invention.

The method and kit of the present invention may also be used to determine different types of damage to the adsorbent. To test for damage other than moisture contamination, the method would further comprise activating the adsorbent sample before running the test as described herein. Activation of the adsorbent sample drives out water contamination from the sample and any performance loss is then attributable to other factors.

The method of the present invention may be modified such that an adsorbent sample could be exposed to moisture during normal use, requiring an activation step. Adsorbents for prepurification units (PPUs) and hydrogen PSAs can be tested using this method. Although other test gases may be used, $CO_2$ is the preferred test gas due to the higher $CO_2$ capacity for the adsorbents typically used in PPUs and hydrogen PSAs and will provide for better test accuracy.

In yet another embodiment of the present invention, the test method could comprise partial displacement of the test gas instead of full displacement of the test gas. For example, if for some reason the adsorbent sample could not be fully saturated by the displacing agent, a portion of the adsorbent could be saturated. If partial displacement is calculated, then the baseline partial displacement must also be calculated for the uncontaminated adsorbent.

The components of the field test kit of the present invention may be substituted with other equipment that serve essentially the same purpose and accomplish the same result. For example, the vessel used to measure the displaced gas in the method and kit of the present invention can be any device that is capable of measuring gas volume. Another example is that the balance could be omitted and replaced with a device to measure out a fixed volume of adsorbent. The results would then be expressed as cc of test gas per cc of adsorbent.

Although the invention has been described in detail with reference to certain preferred embodiments, those skilled in the art will recognize that there are other embodiments within the spirit and the scope of the claims.

What is claimed is:

1. A method of determining gas capacity of an adsorbent material used in a gas separation process comprising the steps of:
    a. taking a sample of the adsorbent material used in the gas separation process and placing the sample in a container means in a controlled environment;
    b. weighing the sample of the adsorbent material in the controlled environment;
    c. measuring the ambient temperature of the controlled environment;
    d. flowing a dry gas into the controlled environment;
    e. adsorbing the gas onto the sample of adsorbent material;
    f. saturating the sample with a liquid displacing agent and displacing the adsorbed gas from the sample of adsorbent material;
    g. measuring the volume of gas released from the sample of adsorbent material; and
    h. determining the gas capacity by calculating the ratio of gas released to the weight of the sample.

2. The method of claim 1, wherein the adsorbent material selected from the group of zeolites, silica and alumina or a combination thereof, and is in the form of beads, pellets or powder.

3. The method of claim 1, wherein the controlled environment is a glove chamber.

4. The method of claim 1, wherein the sample weight is in the range of 1.3 to 1.7 g.

5. The method of claim 1, wherein the dry gas is nitrogen, carbon dioxide, oxygen or air.

6. The method of claim 1, wherein the displacing agent is water.

7. The method of claim 1, wherein the gas separation process is a pressure swing adsorption process, vacuum pressure swing adsorption process, or temperature swing adsorption process.

8. The method of claim 1, wherein the container means is a vial with an airtight septa cap.

9. The method of claim 8, wherein the displacing agent is transferred from a syringe having a capacity of up to 60 cc via a cannula through the septa cap into the vial and wherein the volume of gas released from the sample flows back through the cannula into the syringe and is measured in the syringe.

10. A method of determining the gas capacity of an adsorbent material used in a gas separation process, wherein the gas separation process comprises using one or more adsorbent beds, comprising the steps of:
    a. taking a sample of the adsorbent mat1rial from an adsorbent bed and placing the sample in a controlled environment;
    b. weighing the sample of the adsorbent material in the controlled environment;
    c. measuring the ambient temperature of the controlled environment;

d. flowing a first dry gas into the controlled environment, heating the sample and removing any moisture contained in the sample;
e. cooling the sample and stopping the flow of the first dry gas;
f. flowing a second dry gas into the controlled environment;
g. adsorbing the second dry gas onto the sample of adsorbent material;
h. saturating the sample with a liquid displacing agent and displacing the adsorbed gas from the sample of adsorbent material;
i. measuring the volume of second dry gas released from the sample of adsorbent material; and
j. determining the gas capacity by calculating the ratio of volume of second dry gas released to the weight of the sample.

11. The method of claim 10, wherein the adsorbent material selected from the group of zeolites, silica and alumina or a combination thereof, and is in the form of beads, pellets or powder.

12. The method of claim 10, wherein the sample weight is in the range of 0.3 to 0.4 g.

13. The method of claim 10, wherein the dry gas is nitrogen, carbon dioxide, oxygen or air.

14. The method of claim 10, wherein the displacing agent is water.

15. The method of claim 10, wherein the gas separation process is a pressure swing adsorption process, vacuum pressure swing adsorption process, or temperature swing adsorption process.

16. The method of claim 10, wherein the controlled environment is vial with an airtight septa cap.

17. The method of claim 16, wherein the displacing agent is transferred from a syringe having a capacity of up to 60 cc via a cannula through the septa cap into the vial and wherein the volume of gas released from the sample flows back through the cannula into the syringe and is measured in the syringe.

* * * * *